(12) United States Patent
Sharareh (10) Patent No.: US 12,138,007 B2
(45) Date of Patent: Nov. 12, 2024

(54) SYSTEM FOR IDENTIFYING AND REMEDIATING PATIENT WITHDRAWAL SYMPTOMS

(71) Applicant: Rekovar, Inc., Irvine, CA (US)

(72) Inventor: Shiva Sharareh, Laguna Niguel, CA (US)

(73) Assignee: Rekovar, Inc., Irvine, CA (US)

( * ) Notice: Subject to any disclaimer, the term of this patent is extended or adjusted under 35 U.S.C. 154(b) by 373 days.

(21) Appl. No.: 17/528,721

(22) Filed: Nov. 17, 2021

(65) Prior Publication Data
US 2023/0148863 A1    May 18, 2023

(51) Int. Cl.
| | |
|---|---|
| A61B 5/02 | (2006.01) |
| A61B 5/00 | (2006.01) |
| A61B 5/256 | (2021.01) |
| A61B 5/279 | (2021.01) |
| A61B 90/00 | (2016.01) |
| G16H 20/17 | (2018.01) |
| G16H 40/67 | (2018.01) |

(52) U.S. Cl.
CPC ............ *A61B 5/0022* (2013.01); *A61B 5/256* (2021.01); *A61B 5/279* (2021.01); *A61B 90/39* (2016.02); *G16H 20/17* (2018.01); *G16H 40/67* (2018.01)

(58) Field of Classification Search
CPC ....... A61B 5/0022; A61B 5/256; A61B 5/279; A61B 90/39; A61B 5/01; A61B 5/024; A61B 5/0533; A61B 5/0816; A61B 5/14542; A61B 5/318; A61B 5/363; A61B 5/369; A61B 5/4094; A61B 5/4845; A61B 5/6833; A61B 5/7264; A61B 5/7275; A61B 5/165; A61B 5/7267; A61B 5/7282; A61B 5/4839; A61B 5/681; G16H 20/17; G16H 40/67; G16H 50/20
See application file for complete search history.

(56) References Cited

U.S. PATENT DOCUMENTS

| | | | |
|---|---|---|---|
| 10,529,357 B2 | 1/2020 | Richards et al. | |
| 11,328,738 B2 | 5/2022 | Richards et al. | |
| 2017/0172411 A1* | 6/2017 | Bloch-Salisbury | A61B 5/02055 |
| 2020/0129115 A1* | 4/2020 | Lester | A61B 5/4803 |
| 2020/0187777 A1* | 6/2020 | Luderer | G16H 20/10 |
| 2023/0260535 A1 | 8/2023 | Ingraito et al. | |

* cited by examiner

*Primary Examiner* — Rex R Holmes
(74) *Attorney, Agent, or Firm* — K&L Gates LLP; Brian J. Novak; Dennis A. Majewski (57) ABSTRACT

The invention refers to a system for delivering a machine-learning based behavioral intervention for the care of withdraw symptoms such as Neonatal Abstinence Syndrome in neonates. The system obtains biosensor or behavioral information about a patient from a wearable device on the patient and makes a determinative recommendation or takes appropriate action based on its evaluation. The biosensor and behavioral information is collected by way of a wearable device over progressive periods of time. When the data is indicative of a need for treatment because the patient is exhibiting symptoms or indicating relapse traits, this information is sent to the system for evaluation. When the data is indicative of a need for treatment, action is taken in the form of a recommendation or when the device is configured to support direct treatment, direct action can be taken to modify alleviate the patient.

12 Claims, 7 Drawing Sheets

SYSTEM FOR IDENTIFYING AND REMEDIATING PATIENT WITHDRAWAL SYMPTOMS

BACKGROUND OF THE INVENTION

Field of the Invention

Embodiments of the invention relate to the field of identifying and remediating patient withdrawal symptoms. In neonates or infants, the system identifies Neonatal Abstinence Syndrome (NAS) and in adult patients the system monitors for and identifies withdrawal and/or relapse symptoms. More specifically, one or more embodiments of the invention are directed to a drug delivery management system for managing a patient's drug craving and withdrawal by sensing and monitoring hemodynamic, physiological and environmental data and administering effective amounts of a drug to control or prophylactically treat drug related withdrawal.

Background

In 2017, the U.S. government declared the opioid crisis a public health emergency and called for action to address a rapidly escalating national epidemic of drug use. Physiological dependence can occur after a patient has been consuming daily dosages of opioids (either prescription painkillers or heroin) typically for three weeks or longer. Once physiological dependence is manifest, opioid dosage reduction or complete cessation will cause acute opioid withdrawals. Clinical signs and symptoms of opioid withdrawals include dysphoria, anxiety, restlessness, gastrointestinal distress, tachycardia and flu-like symptoms. Depending on the exact type of opioid that the patient has consumed, these withdrawal symptoms will onset as soon as a few hours after the last opioid intake. Typical durations for opioid withdrawal symptoms range from several days to a few weeks. Untreated opioid withdrawals, albeit rarely life threatening, can be very uncomfortable for the patient and often result in relapse to opioid use.

To break through this vicious cycle, the first step for patients who seek to stop taking opioids is to undergo medically supervised opioid withdrawal, also referred to as "detoxification". There are both inpatient and outpatient facilities available where patients receive medication to reduce the severity of their withdrawal symptoms. Once detoxification is completed successfully, most patients will require a so-called "maintenance treatment" that is long-term in nature in order to prevent relapse. In fact, opioid use disorder is generally a chronic condition (comparable to high-blood pressure or asthma) for which most patients require a life-long "maintenance" treatment (after detoxification), consisting of a medication-assisted therapy (MAT) to suppress drug cravings and relapse.

Currently, the most typical maintenance treatment consists of daily administering either methadone or buprenorphine ("BUP"), accompanied by psychotherapy and drug counseling. In the U.S. methadone is a schedule II controlled substance subject to strict regulatory requirements that limit access and the settings in which the drug can be offered to patients. Buprenorphine on the other hand is schedule III drug that can be prescribed in a clinician's office for both detoxification and maintenance treatment. It is currently available as sublingual tablets (with and without the opioid antagonist naloxone), a passive transdermal patch, an implant that provides a low, steady dose for six months, a long-term injection (duration: 1 month). Both the implant and the injectable formulation are indicated after the patient has achieved clinical stability with sublingual buprenorphine at a daily dose of 8 mg or less. While there are no clinical studies published yet on the efficacy of the long-term injectable formulation, a randomized trial with 163 patients over six months has demonstrated the efficacy of the implant formulation.

Despite such available modalities, there remains concerns regarding the general method of drug administration using a passive, "constant-release" rate implant, patch or injection. Some of these issues have delayed Food and Drug Administration (FDA) approval of the implant which originally was supposed to occur in 2013. For example, the buprenorphine dose is fixed and cannot be adjusted to individual needs. (It is known that doses for effective opioid abuse treatment can vary substantially from individual to individual). Another problem with all long-acting, constant release devices and formulations is the fact that the intensity of opioid withdrawal symptoms and cravings tend to vary greatly with time. It is believed that these alternations are responsible for patients dropping out at alarmingly high rates, both out of detoxification programs and of long-term maintenance programs. For example, a recent study my Morgan et al. have shown that more than 50% of patients on transdermal buprenorphine (BUP) discontinue treatment within 30 days. Long-term studies have shown that after one year, only 10% are still using the transdermal patch.

During detoxification, patients are typically in states of great discomfort, pain and emotional distress. Relapse occurs often because the withdrawal symptoms are too severe and not adequately relieved with medication. Thus, there are currently massive unmet clinical needs in the prevention of relapse during both detoxification and the long-term maintenance treatment. The present invention addresses this need in the art.

DESCRIPTION OF THE RELATED ART

There are currently no known system that provide continuous monitoring, identification and management of withdrawal symptoms in patients. More specifically, there are no existing systems able to monitor for and identify in neonates Neonatal Abstinence Syndrome (NAS) and recommend or provide a reliable drug treatment intervention. There are also no known systems for assisting a recovering drug addict from relapsing.

Generally, the management of withdrawal symptoms or NAS is accomplished through both non-pharmacological and pharmacological interventions. Both approaches help treat and decrease the severity of withdrawal symptoms such as seizures, tachycardia, irritability, sleep problems, high-pitch crying, increased muscle tone, hyperactive reflexes, poor feeding, diarrhea, dehydration, sweating, fever or unstable temperature, rapid breathing. Non-pharmacological treatment methods are generally preferred and seek to decrease the patients exposure to environmental stimuli. When an infant is being treated these treatments may include things like swaddling, rocking, gentle handling, demand feeding, and taking care to avoid waking the infant. New studies are showing both pharmacological and non-pharmacological approaches are key to treating infants with NAS.

Currently neonates or infants diagnosed with NAS who are in need of a pharmacological treatment are sent to a neonatal intensive care unit (NICU) and from there to step-down units (SDUs). Infants admitted in the NICU have a difficult time "rooming in" with mother and require a low stimuli environment. Infants treated in a pediatric unit instead of a NICU tend to require less pharmacological treatment, have a shorter length of stay and there is a reduced overall health cost in an environment that is better suited for the infant.

When no pharmacological treatment is given, NAS infants often died, not only from lack of treatment for NAS, but, in some instances, from prematurity. Once an addiction condition is identified from interruption of the placental supply of opiates, pharmacological interventions result in improved survival rates. Currently the most common medications used for NAS treatment include morphine and methadone with phenobarbital, clonidine, and buprenorphine being used alone or as adjuvant therapy. However, pharmacological management is not standardized. Medication dosing and weaning varies from medical center to medical center, and even from clinician to clinician in the same treatment facility. The threshold for initiating pharmacological intervention is questioned by some clinicians and, if treated, the choice of medication remains controversial.

Treatment of NAS depends upon the clinical presentation of NAS and the patient's response to nonpharmacological and pharmacological interventions. How well a patient responds varies significantly depending upon its gestational age, metabolism, genetic predisposition, and epigenetics. For infants the mother's choices and health matter as well as the infant's treatment depends upon the type, quality, and quantity of any drug the mother used. Whether the mother used selective serotonin reuptake inhibitors (SSRIs) and whether the mother enrolled in Medication Assisted Therapy or was a smoker. External factors such as whether the mother can breastfeed or and room-in with the infant also matter. Unfortunately, significant variability persists in the pharmacological treatment given to infants with NAS and adults experiencing withdrawal symptoms. This variability causes an unnecessary number of patients to suffer or experience fatalities.

To overcome the problems and limitations described above there is a need for a system that can provide continuous monitoring, identification and remediation of withdrawal symptoms to provide an appropriate drug intervention.

BRIEF SUMMARY OF THE INVENTION

One or more embodiments of the invention are directed to a system that provides continuous monitoring, identification and remediation of withdrawal symptoms.

The present invention is directed to a drug treatment platform that enables a successful reduction of withdrawal symptoms (e.g., NAS) by providing a system for early recognition and assessment of withdrawal severity in NAS babies or adult patients. In doing so on an ongoing basis, a more optimized therapy that is provided in small but effective doses is possible. One or more embodiments of the invention are directed to a system for identification and management of opioid withdrawals in neonates at risk of such medical condition. In other embodiments the system is adapted to identify and manage withdrawal symptoms in adult patients. Additional embodiments or if desired the same embodiment may also be used to help a drug addicted patient from relapsing.

There are various components to the system implementing one or more embodiments of the invention. These components may include an interactive technology such as a tablet, an interactive interface such as an app, a device or device(s) for data collection and intervention delivery, and an evaluation system for monitoring patient data and determining when the patient is exhibiting symptoms requiring intervention in a manner that is more effective and more capable than trained medical professionals.

DETAILED DESCRIPTION

One or more embodiments of the invention directed to a system and method for monitoring, identifying, and remediating withdrawal symptoms will now be described. In the following exemplary description numerous specific details are set forth to provide a more thorough understanding of embodiments of the invention. It will be apparent, however, to an artisan of ordinary skill in the art, the present invention may be practiced without incorporating all aspects of the specific details described herein. Furthermore, although steps or processes are set forth in an exemplary order to provide an understanding of one or more systems and methods, the exemplary order is not meant to be limiting. One of ordinary skill in the art will recognize the steps or processes may be performed in a different order, and that one or more steps or processes may be performed simultaneously or in multiple process flows without departing from the spirit or the scope of the invention. In other instances, specific aspects of the invention well-known to those of ordinary skill in the art are not described in detail so as not to obscure the invention. It should be noted that although examples of the invention are set forth herein, the claims, and the full scope of any equivalents, are what define the metes and bounds of the invention.

For a better understanding of the disclosed embodiment, its operating advantages, and the specified object attained by its uses, reference should be made to the accompanying drawings and descriptive matter in which there are illustrated exemplary disclosed embodiments. The disclosed embodiments are not intended to be limited to the specific forms set forth herein. It is understood that various omissions and substitutions of equivalents are contemplated as circumstances may suggest or render expedient, but these are intended to cover the application or implementation.

The term "first", "second" and the like, herein do not denote any order, quantity or importance, but rather are used to distinguish one element from another, and the terms "a" and "an" herein do not denote a limitation of quantity, but rather denote the presence of at least one of the referenced item.

It will be understood that when an element or layer is referred to as being "on," "connected to," or "coupled to" another element or layer, it can be directly on, connected to, or coupled to the other element or layer, or one or more intervening elements or layers may be present.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

For the purposes of this application, the words neonatal, baby, babies, infant, infants may be understood to be interchangeable with each other, unless otherwise specified. The term patient is a reference to any person who is under observation by a medical caregiver for treatment or possible treatment. For example, a patient can be a baby, infant or adult person of any age.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

One or more embodiments of the invention will now be described. As previously noted above, current treatments for withdrawal symptoms such as NAS require the clinical presentation of evident symptoms and the patient must respond to nonpharmacological and/or pharmacological interventions if they are given. There is significant variability in the pharmacological treatment of patients with withdrawal symptoms and not all patients with the condition are recognized as having it leading to an unreasonably high patient mortality rate. The system and methods described herein continuously monitoring the patient, identify withdrawal symptoms and determine an appropriate treatment. This obviates the inherent variability in diagnosis and treatment and thereby improves treatment for patients with withdrawals symptoms such as newborns with NAS. The system can also be used to help drug addicted patients from relapsing as will be more fully described below.

Figure 1:
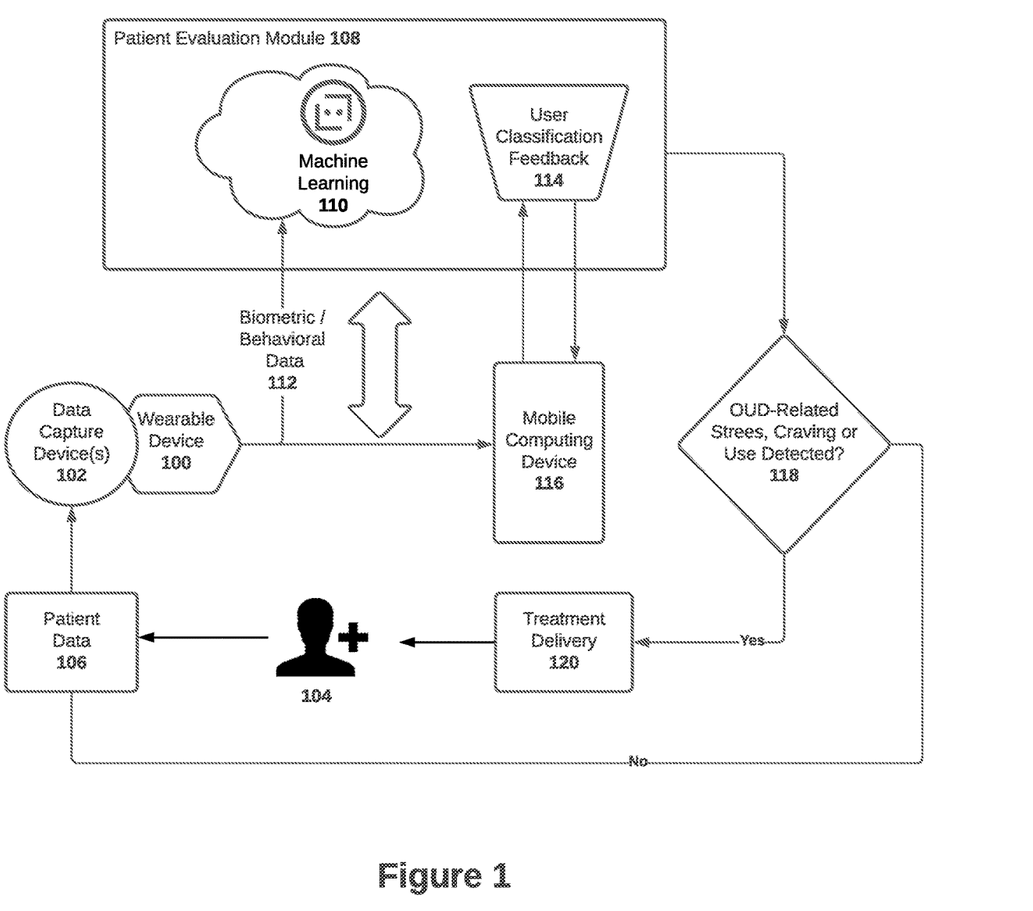
FIG. 1 illustrates a high-level overview of the system for monitoring, identifying and remediating withdrawal symptoms configured in accordance with one or more embodiments of the invention.

FIG. 1 illustrates a high-level overview of the system configured for monitoring, identifying and remediating withdrawal symptoms in accordance with one or more embodiments of the invention. To achieve the desired impact which is to identify, manage and treat patients with withdrawal symptoms such as infants with NAS, embodiments of the invention make use of a wearable device (100) which contains or is connected with, a collection of one or more sensors or data capture devices (102). These data capture devices (102) are configured to obtain information about the condition of a patient (104) which can be an infant or adult at risk of withdrawal symptoms. Wearable device (100) accepts patient data (106) from the data capture device(s) (102) and sends it to a patient evaluation module (108) for processing. These data capture device(s) (102) monitor the patient and collect biomarker data from the sensor or observation inputs. The system collects data about the patient's movement and any audible outputs along with other information subtle enough a trained visual observer would easily miss. These data capture device(s) (102) may be sensors embedded into the wearable device (100) or associated with the wearable device (100). This wearable device (100) is paired in one embodiment of the invention with a camera system that monitors behaviors beyond what sensors can provide. Using the camera system, the system can determine body, hand and foot movement and evaluate facial expressions and other movement related characteristics.

The mobile computing device (116) may be used as a patient portal by caregivers to monitor the journey of patients going through withdrawal symptoms such as infants experiencing NAS or adults experiencing withdrawal symptoms. The mobile computing device (116) may display physiological biometric and/or behavioral data obtained from the wearable device (100). This wearable device is typically a wristwatch type device with built in sensors. The system may optionally also make use of a chest hub or other wearable devices designed to obtain biometric data from the patient and work in conjunction with the wristwatch. The chest hub may have a wireless communication capability so the device can communicate with the mobile computing device (116), a drug pump, patch, and/or the data capture devices. The chest hub may have an integrated devices such as a drug pump, respiratory sensor, electrocardiogram (ECG) device and skin temperature monitor for monitoring the patient's withdrawal symptoms and determining a recommended drug intervention. By using the data such as the ECG, heart rate, and/or temperature the system can predict when a seizure may take place. The combination of various measurements and the correlated sensor information provide seizure predictive analytics that may be used in combination the other features described herein. An EEG may be incorporated into the system to enable seizure detection. A camera system for observing the patient's movement may also be incorporated into one or more embodiments of the invention. The EEG data and the camera image data either alone or in combination are evaluated by the system to determine when the patient is undergoing or may be undergoing a seizure.

The system may include a wearable device such as a monitoring device attached to the patient or one that is otherwise able to monitor the patient. For example, a wearable wrist patch containing sensors able to measure physiological biomarkers such as lactate, sweat, tissue oxygenation, and/or movement among other things is incorporated into the system in one or more embodiments of the invention. When used, the wrist patch may wirelessly transmit the information it gathers to the system.

The wearable device (100) and/or the mobile computing device (116) may display warning alarms if the patient needs drug intervention or other treatment. The system may obtain and record a patient assessment of symptoms on an ongoing basis or at desired time intervals. Some non-limiting examples of symptoms displayed on the mobile computing device (116) include seizures, tachycardia, irritability, sleep problems, high-pitch crying, tight muscle tone, hyperactive reflexes, poor feeding, diarrhea, dehydration, sweating, fever or unstable temperature, rapid breathing. The mobile computing device (116) is in communication with the wearable device (100) via a network. The network may be wireless or wired in any way that enables the devices to readily communicate with one another. The biometric and/or behavioral data obtained by the wearable device (100) via data capture device(s) (102) is communicated to the mobile computing device (116) through this network connection.

The biometric and/or behavioral data is processed by the patient evaluation module (108) which is also connected to the network in one more embodiments of the invention. The patient evaluation module (108) is typically where data processing and machine learning algorithms evaluate the biometric and/or behavioral data however the functionality of the patient evaluation module (108) may also be implemented on mobile computing device (116) or in the cloud in whole or in part.

Further detail about the operability and functionality of the patient evaluation module (108) follows below in FIG. 2. The patient evaluation module (108) utilizes a machine learning component (110) to process and classify biometric and/or behavioral data (112) as falling within parameters indicative or not of NAS withdrawal symptoms or adult withdrawal symptoms. Results of the machine learning component are optionally subject to user classification feedback (114), which is typically input via the mobile computing device (116) or via any other input means.

This expert user feedback enables the system to learn which inputs are indicative of NAS withdrawal symptoms or adult withdrawal symptoms. The biometric and behavioral data (112) is sent to an algorithm, which can be, for example, a supervised machine-learning algorithm such as a support vector machine with convoluted neural networks to determine which symptoms of NAS are active and assess the level of severity of the NAS. Implementing this type of multimodal dataset provides a novel approach for detecting withdrawal symptoms and behaviors of interest based on convolutional neural networks (CNN) and support vector machine (SVM). This is accomplished using a system such as Tensorflow or some other machine learning platform. Once the data has been collected through the data capture devices such as a wristband and/or camera system, and validated by a clinician and psychometrician, the system uses this data to construct large sample sets of different kinds of non-withdrawal and withdrawal-based symptoms and behaviors as the positive and negatives of each sample set. This enables the system to identify the region of interest (ROI). These may be initially validated with a biostatistian. A convolutional neural network with a support vector machine (CNN-SVM) filters the results of the extracted data to reduce the number of negative ROI. Multiple convolutional layers are used to train the dataset to construct the neural network. SVM provides a replacement for the fully connected layer while a softmax classifier is used to classify the sample set based on the training model in order.

As will be more fully described herein, this automated assessment produces a score. Depending on how high the score is and what categories are scored, medication dosage or non-pharmacological treatments are suggested to the doctor/nurse's software screen to show which treatment is most appropriate and possibly most effective. This is the output in one or more embodiments of the invention. In other embodiments of the invention the system contains devices enabling the system to also deliver the treatment to the patient as the output. These outputs are produced from the inputs received from the sensors (biometrics) and camera data (behavioral patterns). These inputs are processed by the machine learning algorithm which can determine an appropriate course of action based on the patient data.

The mobile computing device (116) provides an interface for a user to review the biometric data (112) results and/or to provide user classification feedback (114). Once the patient evaluation module (108) classifies the biometric data (112) and permits the data to be subject to the optional user classification feedback (114), a determination is made as to whether the patient is experiencing opioid use disorder (OUD)-related stress, craving or use (118). If an OUD is identified, the system identifies, recommends and/or delivers an appropriate treatment regime (120) for the patient (104). If an OUD is not identified, the system continues to monitor patient (104) and the patient's corresponding date is captured via data capture device(s) (102).

The mobile computing device (116) performs the functionality described herein via a software application. This software application has access to a patient's biometric and/or behavioral data and enables caregivers to observe and access the patient's data via a mobile tablet, phone or other mobile computing device. This provides an interface for continuously monitoring the patient. For infants that are moved outside of a Neonatal Intensive Care Unit (NICU) setting this is particularly important as such monitoring does not normally occur outside of a NICU setting. The software application also provides parents or any other permitted user with a way to remotely monitor their baby and vitals.

Figure 2:
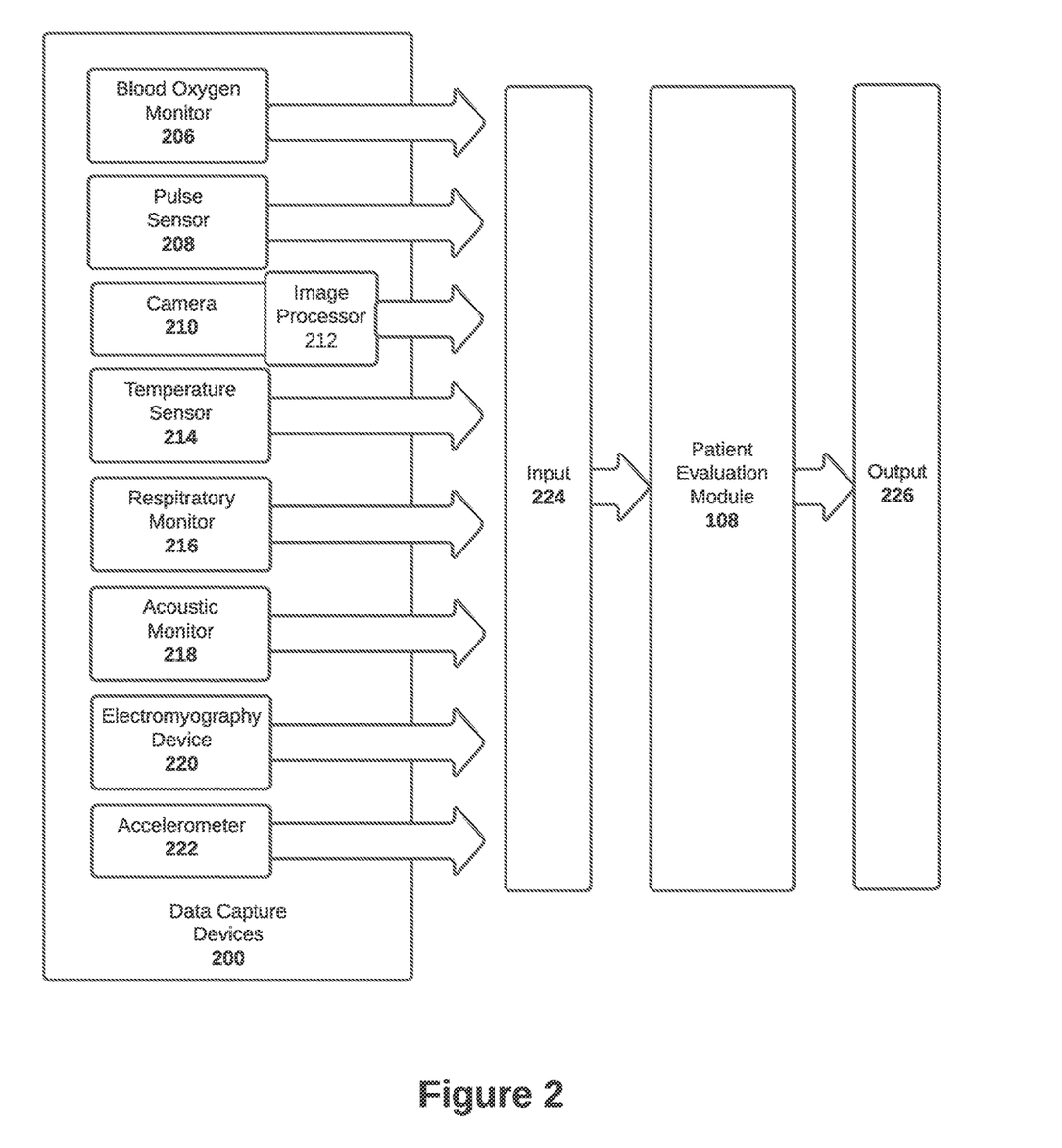
FIG. 2 illustrates an assortment of data capture devices utilized in accordance with one or more embodiments of the invention.

FIG. 2 illustrates an assortment of data capture devices utilized in accordance with one or more embodiments of the invention. The data capture devices are represented in diagram block (200). Various types of data capture devices (200) are contemplated as being within the scope of the invention. These data capture devices may be incorporated into the wearable device (100) and/or configured to obtain data independently and provide it to the patient evaluation module (204) as an input (202). The type of data capture devices contemplated by the invention are those configured to collect useful information about the health status of a patient. The patient can be an infant when the system is configured to identify NAS withdrawal symptoms, but embodiments of the invention can be adapted to evaluate patients generally and other symptoms as well based on data received from the data capture devices (200). Systems implemented to identify withdrawal symptoms such as NAS or OUD, contain at least one or more of the following types of data capture devices: a blood oxygen monitor (206), a pulse sensor (208), a camera (210) with an image processing module (212) configured to detect body movements, a temperature sensor (214), a respiratory monitor (216), an acoustic monitor (218), an electromyography device (220), and/or an accelerometer (222) for detecting movement. Each of these data capture devices (200) obtains biometric and/or behavioral data about the health of the patient. The blood oxygen monitor (206) measures the level of oxygen in the patient's blood. The pulse sensor (208) determines the patient's heartrate. The system may also contain a device for determining blood pressure. The camera (210) is configured to capture images (video and/or still images) of the patient. These images are used to assess whether the patient is experiencing withdrawal symptoms such as NAS or OUD. Once images are captured an image processing module (212) determines whether the patient is exhibiting NAS and/or OUD characteristics. The image processing module can, for example, observe and determine the patient is experiencing body movements that would be characterized as restless or out of the ordinary for a normal patient or infant. As a non-limiting example, the camera (210) may capture facial expressions and body, hand and/or foot movement and image processing module can characterize what a nurse may not be able to observe as the device is with the patient 24 hours a day whereas a nurse cannot typically stay with a patient for such a duration. The camera (210) may also capture subtle movements or behaviors that might otherwise not be ascertained from visual observation. The camera may for example identify instances of patient restlessness, seizure or other movement related symptoms.

The temperature sensor (214) measures the temperature of the patient. The respiratory monitor (216) measures a patient's respiration rate and can typically measure heart rate as well. The acoustic monitor (218) monitors the decibel level of the patients and can detect subtle differences in frequency that an untrained human ear cannot typically detect. For example, in one embodiment of the invention the acoustic monitor (218) determines the difference between an infant with an excessively high-pitched cry vs high pitched cry. The electromyography device (220) determines the health of the patient's muscles, and the motor nerve cells that control them and can thereby reveal nerve dysfunction, muscle dysfunction or problems with nerve-to-muscle signal transmission. The accelerometer (222) measures movement of the patient and aids in detecting how frequent and to what extents a patient is moving about and/or the patient's general level of restlessness.

The biometric and/or behavioral data obtained from the data capture devices may be stored on a wearable device, mobile device, on a remote data source or local computer so it may be utilized as needed to achieve the purpose of the invention. Embodiments of the invention may utilize additional data capture devices in situations where additional information contributes to determining a diagnosis or the health of the patient. These data capture devices are intended to accurately and continuously or at least at regular intervals capture the biomarkers specified in the Finnegan Neonatal Abstinence Score (FNAS). Every data capture device described herein is not required to implement the invention and systems may utilize a select one, a select few devices or all devices as input (224) to accomplish the goal of determining if a patient is undergoing withdrawal symptoms. Also, the functionality of the various data capture devices may be combined into a unit with such functionality or be contained in separate devices. Generally speaking, having more inputs (224) increases the diagnostic accuracy but the addition of some inputs are less significant than others and all inputs are not required. Inputs may be added or subtracted based on determinations made by the patient evaluation module (108). Once the patient evaluation module (108) performs its analysis, an output (226) is generated. This output (226) is a probabilistic diagnosis made based on the input(s) (224) about whether the subject patient is experiencing withdrawal symptoms such as NAS, OUD or other symptoms.

Figure 3:
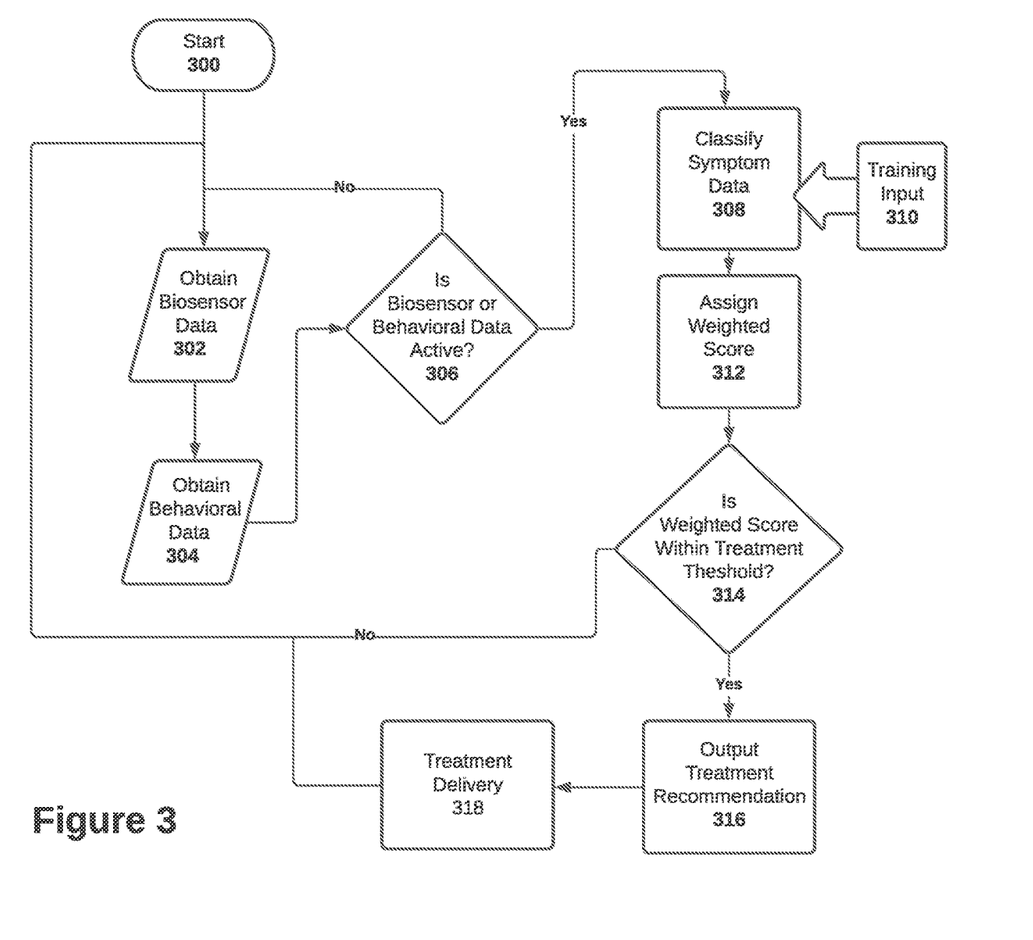
FIG. 3 illustrates the functionality of the patient evaluation module in accordance with one or more embodiments of the invention.

FIG. 3 illustrates the functionality of the patient evaluation module (108) in accordance with one or more embodiments of the invention. The evaluation process starts at start block (300) where the system is powered on and ready to begin processing data. Biosensor data (302) and behavioral data (303) is obtained by devices able to measure such data and provided to the patient evaluation module (108). A wristwatch, chest hub and/or other wearable device(s) having one or more of the data capture devices described in FIG. 2 is one manner this input data may be obtained. The biosensor data (302) is data obtained from any device configured to obtain biological information from the patient or about the patient. The behavioral data (303) is obtained from data capture devices able to visually observe the patient and make a determination about the patient's observed behavior. For example, the camera (210) may capture images and/or video of the patient's movement and using image processor (212) determine the patient is restless, unable to sleep, and/or experiencing other behaviors indicative of withdrawal symptoms. When at least one of the data capture devices is active and has biosensor or behavioral input to evaluate (306), the patient evaluation module (108) evaluates this input data to determine how the data is to be classified (308).

This evaluation system may utilize predictive analytics that improve upon current assessment tools for NAS such as Finnegan Neonatal Abstinence Score (FNAS). These predictive analytics accurately capture symptoms the patient is having while undergoing NAS or withdrawal, predict appropriate treatments and determine what medication and what dosage to administer to the patient to treat the withdrawal assessment.

To improve upon the predictive abilities of the system, the system may utilize a classification process, and receive training inputs (310) from an expert user. Artificial intelligence ("AI") algorithms are utilized when appropriate as part of the evaluation, classification and/or weighting steps. So the system may determine if the input data, falls within a score indicative of there being a need for treatment, a weighted score is assigned (312). If this weighted score (312) falls within a treatment threshold, the system outputs a recommendation for treatment (316) of the withdrawal symptoms. Treatment delivery (318) then begins, and the system continues to actively monitor the progress of the patient by continuing the process. Treatment delivery may occur by an automated means in one or more embodiments of the invention or by a physically administered means in other instances.

As a treatment delivery solution, embodiments of the invention may utilize a medication cartridge/patch with active drug release capabilities. The medication patch is typically a microneedle patch and drug reservoir that may be attached to the skin or a wearable device so the drug can be administered in dosages the system determines to be appropriate. The patch may be refilled by a connected micro pump. The medication/treatment administration need not be automatic but rather may include the approval/acknowledgement from a doctor first before the medication/treatment is administered. In alternative embodiments of the invention, the medication is automatically delivered based on the systems determination of the patient's need. When a drug delivery platform is part of the treatment delivery, the system determines what drug delivery approach to use based on the severity of withdrawal symptoms, as determined by the weighted score generated by the system. When the patient exhibits NAS or OUD characteristics the system can recommend a treatment or administer treatment.

The treatment delivery system may have a closed loop feedback system or open loop feedback system. The closed-loop feedback system for selecting and administering specific medications to patients (e.g., neonates or adults) may administer, in a controlled manner, with frequencies and doses determined by a separate control unit. The open-loop feedback system is able to select and administer specific medications to patients, in a controlled manner, with frequencies and doses determined by a caregiver.

The system may interface with blockchain drug traceability systems and patient monitoring/electronic health record for secured data processing.

Figure 4:
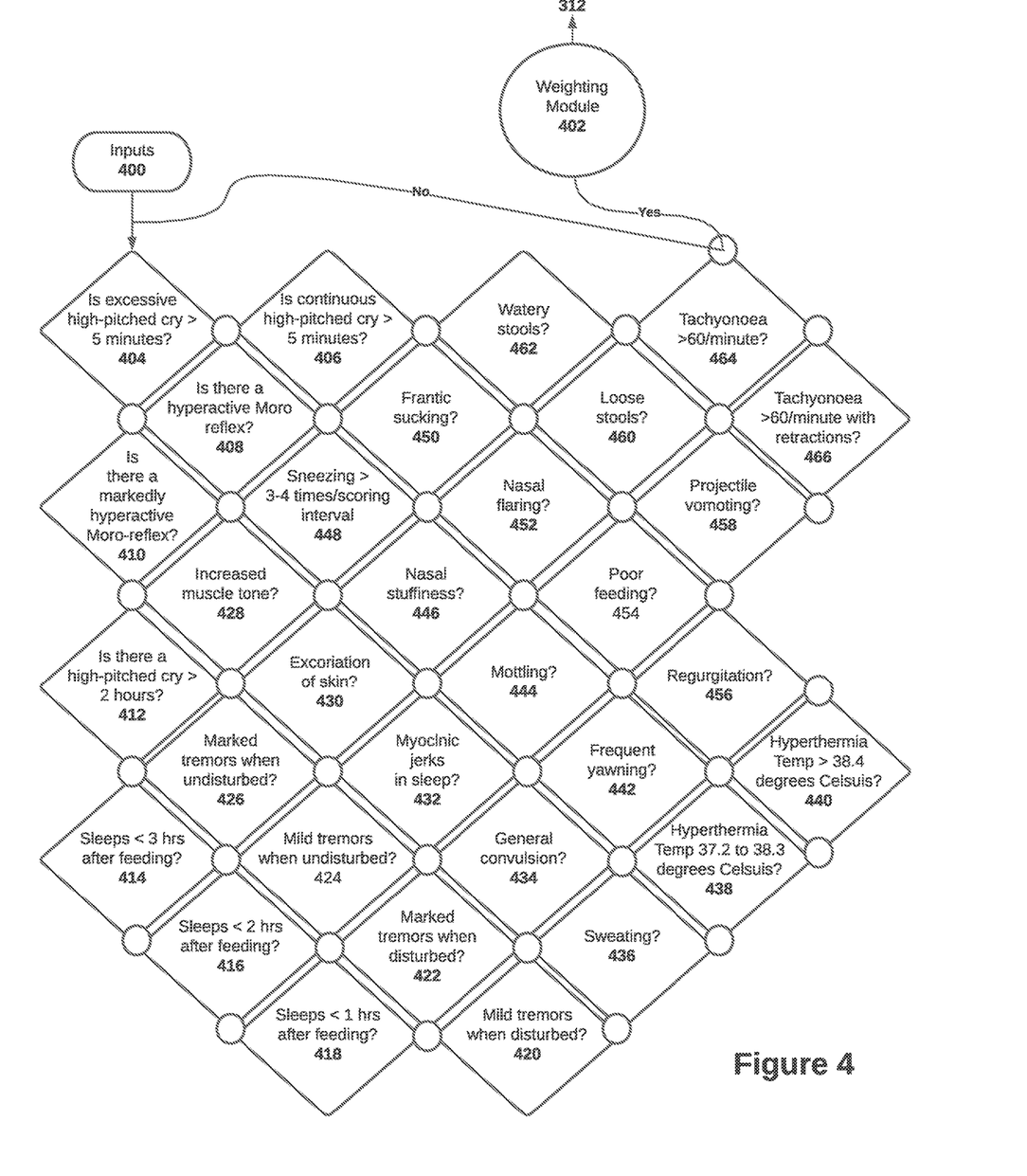
FIG. 4 illustrates how the weighting module functions in accordance with one or more embodiments of the invention.

FIG. 4 illustrates how the weighting module functions in accordance with one or more embodiments of the invention. The weighting module (402), which is responsible for assigning the weighted score (312), obtains as input (400) the classified data obtained from the data capture devices. The weighting module (402) is configured to evaluate this input data and determine based on the symptom, a score weight. The exemplary table below, provides an example of the symptoms the system monitors and when the symptom occurs, a score weight is assigned to the symptom.

| Symptom | Score Weight |
|---|---|
| Excessive High-pitched (or other) cry < 5 mins (404) | 2 |
| Continuous high-pitched (or other) cry > 5 mins (406) | 3 |
| Hyperactive Moro reflex (408) | 2 |
| Markedly hyperactive Moro-reflex (410) | 3 |
| High-pitched cry > 2 hours (412) | 3 |
| Sleeps < 3 hrs after feeding (414) | 1 |
| Sleeps < 2 hrs after feeding (416) | 2 |
| Sleeps < 1 hrs after feeding (418) | 3 |
| Mild tremors when disturbed (420) | 1 |
| Marked tremors when disturbed (422) | 2 |
| Mild tremors when undisturbed (424) | 3 |
| Marked tremors when undisturbed (426) | 4 |
| Increased muscle tone (428) | 1 |
| Excoriation of skin (430) | 1 |
| Myoclonic jerks in sleep (432) | 3 |
| Generalized convulsion (434) | 5 |
| Sweating (436) | 1 |
| Hyperthermia: Temperature 37.2-38.3° C. (438) | 1 |
| Hyperthermia: Temperature >38.4° C. (440) | 2 |
| Frequent yawning (442) | 1 |
| Mottling (444) | 1 |
| Nasal stuffiness (446) | 1 |
| Sneezing (>3-4 times/scoring interval) (448) | 1 |
| Frantic sucking (450) | 1 |
| Nasal Flaring (452) | 2 |
| Poor feeding (454) | 2 |
| Regurgitation (456) | 2 |
| Projectile vomiting (458) | 3 |
| Loose stools (460) | 2 |
| Watery stools (462) | 3 |
| Tachypnoea >60/minute (464) | 1 |
| Tachypnoea >60/minute with retractions (466) | 2 |

These weighted scores are fed into the system so a determination can be made whether the patient is experiencing withdrawal symptoms such as NAS. By utilizing specific input from the data capture devices, the system avoids the problem of widespread variation in the scoring which is what happens when nurses or other medical care professionals are left to draw conclusion about the patient based on observation only. Whether a cry is "high-pitched" for example, is a matter of subjective opinion without decibel information. The system described herein is much more accurate than any human is capable of because the system has quantitative information and can conduct continuous monitoring of the patient in a manner a human cannot. The system can, for example, classify a cry as high-pitched once the frequency of the cry surpasses 800 Hz. A normal cry is 300-500 Hz.

Utilizing the system and methods described herein one or more embodiments of the invention optimize a drug treatment therapy regime in a way previously not feasible. Having a system able to accurately and continuously monitor patients for withdrawal symptoms, assess the withdrawal severity and recommend or initiate a treatment enables the system to save lives and avoid the kind of subpar care patients with symptoms such as NAS withdrawal symptoms presently experience.

Another aspect of one or more embodiments of the invention is focused on monitoring for drug relapses. This embodiment provides a drug treatment platform that enables a successful reduction of relapses by early recognition and assessment of withdrawal severity followed by swift administration of a drug of choice such as buprenorphine (BUP) or other appropriate drugs in small but effective doses.

This embodiment of the invention can detect a patient's physiological biomarkers and environmental activities and responding by applying responsive therapeutic modalities to manage drug craving or prophylactically treating a patient to prevent or mitigate risk of occurrence of relapse. In one or more embodiments of the invention, the system is capable of observing clusters of parameters and based on such parameters recommends a therapeutic intervention such as warning the patient of a dosing time or automatically administering an effective amount of drug to mitigate the risk of relapse. The physiologic biomarkers may include those associated with opiate withdrawal such as dysphoria, anxiety, restlessness, gastrointestinal distress, tachycardia and flu-like symptoms.

In another aspect, the invention optimizes the variability of absorption of a drug to a subject when administered to address patient's need according to her or his individualized needs. Thus, the amount administered is controlled based on an actual physiological need versus a dosage that is just set by a physician or decided upon by the patient.

As the term is used here, "invasively" means any type of administration, which induces at least a temporary breach in the skin of the subject, including any type of parenteral administration, which, for example, may include, but is not limited to, an intravenous administration or any type of injection or infusion whether subcutaneous, intradermal, transdermal, intramuscular, intraperitoneal, intrathecal and the like. For the non-limiting, illustrative purposes and ease of the following description only, the below described embodiments relate to administration of a drug using a pump, for example, a patch or a microinfusion pump, as described herein. In some embodiments, the infusion pump can be connected to the subject on a continuous basis. As can be understood by one skilled in the art, the pump can be connected to the patient subject in any other desired way. Some embodiments of the present application can be used with transdermal drug delivery as well, although some types of transdermal drug administration can be used for temporarily breaching the skin of the subject.

In one or more embodiments of the invention, a drug delivery device can be combined with at least one sensor for measuring parameters that can influence patient's behavior, patient's drug craving, patient's mood and behavioral controls, as well as the drug's pharmacokinetics and/or pharmacodynamics, including, for example, skin temperature, ambient temperature, physical activity, local blood perfusion at the drug infused tissue region, and/or others. Embodiments of the invention can include one or more additional sensors that measure the above and any other parameters that can influence drug's pharmacokinetics and/or pharmacodynamics. In some embodiments, the measured parameters can be used by a controller to calculate an adjustment to the delivered drug dose or rate in order to improve the accuracy and/or the repeatability of the desired effect of the delivered drug. The system contemplates usage of both methadone or other alternatives such as BUP or any other acceptable treatment dependent upon whether administration of the drug has appropriate medical personnel to handle management of the dosages which would be required for methadone vs permitting the patient or the system to automatically handle dosing when a prescription is given.

For example, with regard to BUP, the controller can use the measurement information to calculate an adjustment to the delivered dose or rate or delivery profile in order to improve accuracy or repeatability of the effect. This measurement information can, for example, be used to reduce craving variations during a particular time (e.g., a day). The measurement information can also be used to determine specific times where a patient may experience symptoms of withdrawal such as perspiration, increase heart rate, sweating, hallucination, or other individually identified behaviors. In one or more embodiments, one or more sensors can be disposed at the skin to measure degree of sweating, skin temperature or heart rate. In at least one embodiment, the invention relates to a method for managing craving and behavioral attributes related to opiate or any drug withdrawal. The method includes measuring at least one parameter selected from the group consisting of: physiological, biochemical, environmental, and a parameter related to the drug itself, and adjusting at least one aspect of administration of the drug according to the at least one parameter.

The term "drug", as used herein, is defined to include any pharmaceutically active compound including but not limited to compounds that treat diseases, undesirable symptoms, and improve or maintain health and prolong drug free life.

Implementation of the methods and apparatus described in the present disclosure involves performing or completing certain selected tasks or steps manually, automatically, or a combination thereof. Moreover, according to actual instrumentation and equipment of some of the embodiments of the methods and apparatuses of the present disclosure, several selected steps could be implemented by hardware or by software on any operating system of any firmware or a combination thereof. For example, as hardware, selected operations of the methods, apparatuses, systems and devices described herein could be implemented as a chip or a circuit. As software, selected operations could be implemented as a plurality of software instructions being executed by a computer using any suitable operating system. In any case, selected operations of the method and system of the present disclosure could be described as being performed by a data processor, such as a computing platform for executing a plurality of instructions.

Although the present disclosure is described in relation to a "computer" or a "computer network", it should be noted that any device featuring a data processor and/or the ability to execute one or more instructions may be described as a computer, including but not limited to a PC ("personal computer"), a server, a minicomputer, a cellular telephone, a smart phone, a PDA ("personal data assistant"), a pager. Any two or more of such devices in communication with each other, and/or any computer in communication with any other computer, may comprise a "computer network".

In one or more embodiments of the invention include long-term maintenance treatment, since the cause for relapse is not related to withdrawal symptoms, the system provides for a predictive modeling based on artificial intelligence algorithms that may be used to generate prediction profiles from previous behavioral data that was acquired from a large set of patients. In such an embodiment, a patient memory capturing of "getting high" and feeling "pleasure" often triggered by environmental factors generates cravings that ultimately leads to relapse. As such, healthcare provider, including physicians can use predictive algorithms to establish accurate predictions regarding the therapeutic outcome for the individual patients.

In certain embodiments of the invention, integrated devices are described including sensing, monitoring, processing and drug delivery capabilities which controls both a therapeutic outcome of short (i.e. detoxification) and long-term drug addiction treatment. The platform used in one or more embodiments of the invention, provides around-the-clock monitoring of critical physiological signals ("biomarkers") that quantify the severity of withdrawal symptoms. State-of-the-art sensors can be used that enable minimally invasive monitoring of patient's biomarkers. In one embodiment, a smartphone-like integrated platform for acquiring physiological and external (e.g. GPS location and visual) data in conjunction with a wireless communication system to connect to health care providers are described to provide a real-time monitoring of the patient's risk of relapse while allowing the healthcare provider to determine and initiate the clinically suitable response. The system can also ascertain when a patient has relapsed so that professionals can monitor the patient's status.

Figure 5:
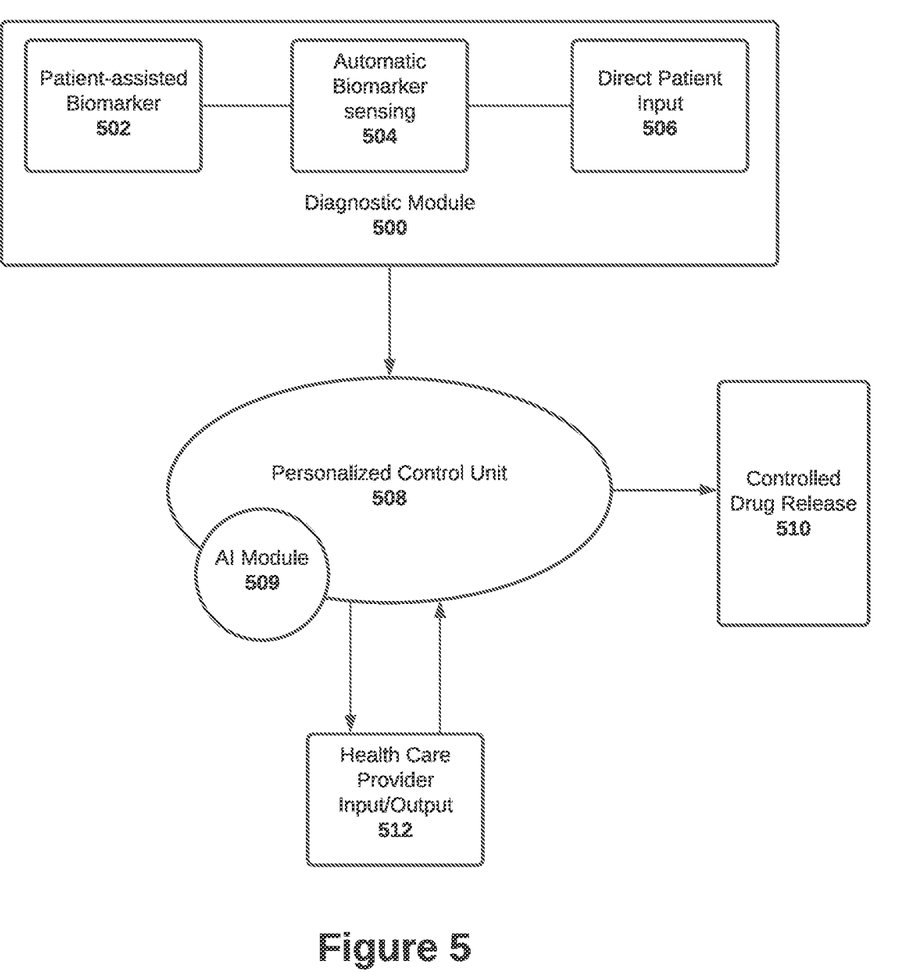
FIG. 5 is a schematic diagram of an exemplary drug delivery system configured in accordance with one or more embodiments of the invention to manage patient drug relapses.

FIG. 5 is a schematic diagram of an exemplary drug delivery system configured in accordance with one or more embodiments of the invention to manage patient drug relapses. As shown, the system can include a patient and provider input system allowing the patient unit control to designate suitable drug delivery. Module 1 is a diagnostic module (500) configured to sense specific biomarkers and provide an input interface. The diagnostic module contains a patient assisted biomarker sensor (502), an automatic biomarker sensor (504) and may also include a patient input device (506), such as a smartphone-like device with imaging and GPS tracking capability, to allow the patient to directly input information. Module 2 is the personalized control unit (508) where all input data is stored, processed and evaluated. This personalized control unit (508) controls the drug release system (510) and communicates wirelessly with health care professionals (512). The personalized control unit (508) may incorporate an artificial intelligence ('AI') module (509) that evaluates the data provided by the diagnostic module (500) and helps inform the recommendation or decision making of the personalized control unit (508). In at least one embodiment of the invention, the diagnostic module (500) acquires a plurality of real-time data sets that reflect critical physiological information about the patient's withdrawal symptoms as specified in the Clinical Opiate Withdrawal Scale (COWS). In one example, the data originates from three separate input pathways: (1) Multiple automatically recorded physiological signals, using non-invasive sensors and skin probes, including the following: photoplethysmograph (PPG), Galvanic skin response (GSR), temperature, and accelerometer, (2) Patient-initiated measurements, e.g. facial imaging and recordings of the eye and nose, using a special smartphone application, (3) a short smartphone-based behavioral evaluation to assess the severity of psychological withdrawals (anxiety, irritability, depression, dysphoria, etc.).

Figure 6:
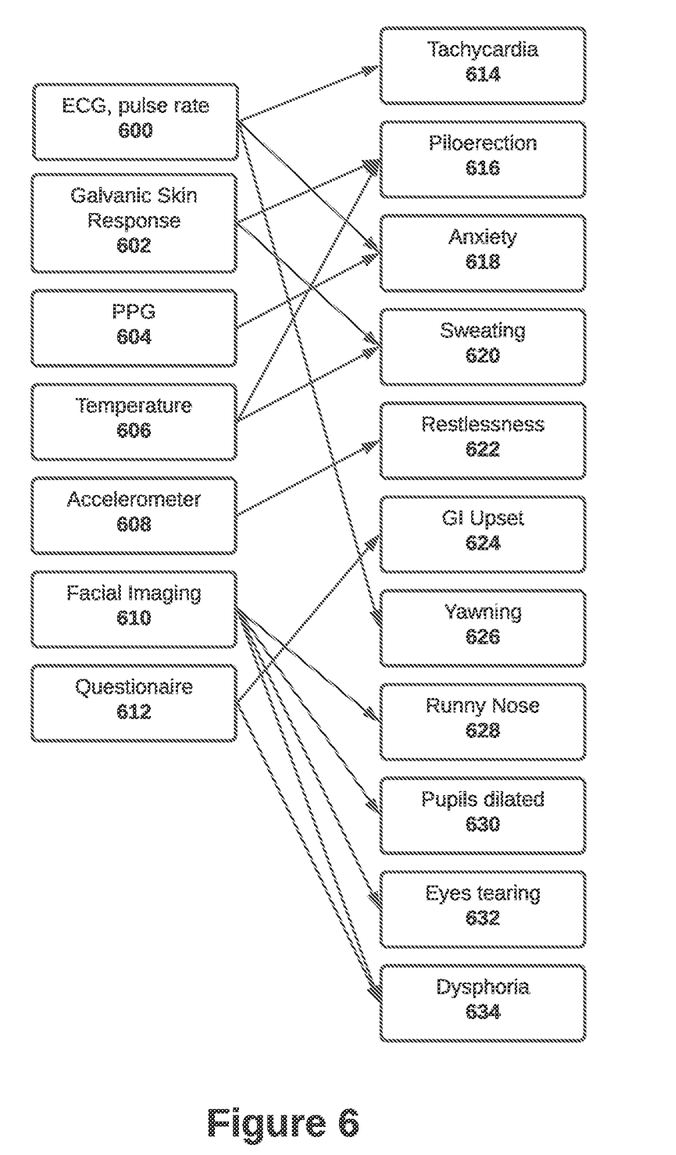
FIG. 6 is a schematic illustration of the typical sensors utilized to assess patient withdrawal and/or relapse symptoms.

FIG. 6 is a schematic illustration of the typical sensors utilized to assess patient withdrawal and/or relapse symptoms. In the example given, which is not meant to be exhaustive or at all limiting of what is monitored on the patient the data the sensor obtains can indicate symptoms the patient is experiencing. For example, the ECG, pulse rate (600) sensor data may indicate the patient is experiencing tachycardia (614), anxiety (618) or yawning (626). The galvanic skin response data (602) may indicate the patient is having a piloerection (616) or sweating (620). PPG (604) data may indicate patient anxiety. Temperature data (606) may indicate a piloerection or sweating (620). The accelerometer (608) data may indicate restlessness (622). Facial imaging (610) data may indicate the patient is experiencing runny nose (628), dilated pupils (630), eyes turning (632) and/or dysphoria (634). A questionnaire (612) presented to the patient for responses may inform the patient is experiencing an upset gastrointestinal (624) tract or dysphoria (634).

The personalized control unit utilizes a microprocessor to processes and analyze these multiple data sets from the diagnostic module and/or questionnaire. The implemented software algorithm in this personalized control unit will ultimately compute the type and dosage of medication to be released through the controlled drug release system (510).

This controlled drug release system provides a delivery system that administers a given dose of BUP in a precise, well-defined way. Optionally, additional medications (e.g., naltrexone, naloxone, clonidine) or select nutrient solutions can be administered. Medications are supplied in disposable, prefilled drug cartridges for tamper-resistant single use. The system uses a micropump that delivers medication through either a catheter or a microneedle patch to an area around the skin where the patch is attached. The pump may be a treatment option if all other traditional methods have failed to relieve the patient's long-term symptoms. Because the medication is delivered directly to the systemic circulation, the withdrawal symptoms can be controlled with a much smaller dose than is needed with oral medication. The goal of a drug pump is to better control the patient's symptoms and to reduce oral medications; thus reducing their associated side effects as well as withdrawal.

The pump is typically a metal or a plastic disposable device about the size of a hockey puck that is surgically implanted beneath the skin of the patient's abdomen or externally outside of the abdomen with a catheter connected and inserted through the skin. A small plastic tube, called a catheter, is surgically placed in the interstitial space and is connected to the pump. A space inside the pump called the reservoir holds the medication. The space can hold up to numerous reservoirs according to size and shape for all the nutrient and health balance deficiency that is needed for the patient. The patch is also connected to the pump via a delivery system such as micro needles. The micro needles can be either passive or active to drive the drug into tissue via a positive pressure placement pump or actively being charged via a wireless method to drive the fluid inside the tissue.

In one or more embodiments of the invention, the pump is programmed to slowly release medication over a period of time. The pump may also programmed to release multiple other medications such as vitamins as well as other inflammatory drugs for reducing the side effects of withdrawals. It can also be programmed to release different amounts of medication at different times of the day, depending on your changing needs. In other embodiments of the invention, the pump stores the information about the patient's prescription in its memory, and the healthcare provider can easily review this information to individualize the drug delivery per patient's historical needs. In scenarios, when the reservoir is empty, authorized health care providers can refill the pump by inserting a needle through your skin and into the fill port on top of the reservoir.

In one or more embodiments of the invention, the infusion pump is wirelessly connected to an external hardware unit with touchscreen interface compatible with the pump. A helpful workflow guide may be provided with simple steps for refill the pump. In other embodiments of the invention, the system contains a built-in device able to do auto-calculations for volume and rates or it provides a way to enable the patients or the healthcare provider to adjust administration parameters. The system further provides visuals accompany prime bolus and flex dosing to help simplify the process. Various communicators and programmers are designed to wirelessly connect enabling flexible and comfortable delivery of patient care within a desired space.

In one or more embodiments of the invention, the device is not limited to a single medication, but may be expanded to carry several substances in individual cartridges for separate, controlled delivery.

In a specific embodiment, a system is described to prevent the devastating psychological consequences that relapse has for many patients. A device according to this aspect of the invention is less invasive as it is intended to be worn for much longer periods of time (possibly for many years). An integrated smartphone platform, allows the patient to have access to customized survey tools in an online platform designed to enhance accountability and provide patients and stakeholders with the opportunity to monitor, track and provide early intervention for noncompliance. In this embodiment, the patient/device interface allows the health-care providers to make real-time behavioral diagnoses. However, as part of an integrated therapeutic device of the one or more embodiments of the invention, an online support platform grants authorized users, healthcare providers or other designated care providers to release additional doses of the drug of choice, (ex. BUP) quasi instantly, an often psychologically devastating relapse from maintenance treatment can be avoided. The mathematical algorithm that suggests if BUP and in what dose should be released, is based on artificial intelligence, it takes the entire patient's history with this device and the outcomes of past interventional drug releases etc. into account. At the same time, health care providers will be able to override the "decision" of the control unit.

In one or more embodiments of the invention, a drug delivery system can be configured to deliver a drug to a patient in coordination with a physiological parameter of the patient (e.g., the patient's heart rate, piloerection, anxiety levels, sweating, restlessness, GI upset, yawning, dilated pupils, eye tearing, dysphoria, body temperature, or respiration rate). In some embodiments, a drug delivery system can be configured to use a combination of infusion and aspiration to control delivery of a drug to a patient. Catheters, controllers, and other components for use in the above systems are also used, as are various methods of using such systems.

In one or more embodiments of the invention, a drug delivery system includes a microcatheter having at least one fluid lumen; a pump configured to infuse fluid through the catheter; a sensor configured to measure a physiological parameter of a patient; and a controller that controls the pump to coordinate infusion of a drug through the catheter with the physiological parameter measured by the sensor.

In at least one embodiment of the invention, the controller can harmonize drug administration and frequency with patient's natural physiological parameters and in accordance to modification of such parameters when patient is at risk of relapse, or craving. In at least one embodiment of the invention a computer an artificial intelligence can automatically configure the patient specific parameters as historically measured by the sensor to trigger a drug administration inquiry to an authorized health care provider of record. The controller can, in one or more embodiments of the invention, synchronize administration based on a cluster of parameters prioritized by patient's specific physiological response before or after an episode of craving.

In at least one embodiment of the invention, the controller can be operable in a learning mode in which no administration is performed, and the controller establishes a correlation between the preidentified biomarkers and patient's physiological state. The system can include an implantable infusion port in fluid communication with the microcatheter. The microcatheter can include first and second fluid lumens. The controller can be configured to control the pump to alternately aspirate fluid through the first fluid lumen and infuse fluid through the second fluid lumen in coordination with the physiological parameter measured by the sensor.

The method of delivering a drug to a patient may include inserting an implantable pump or patch with or without a microcatheter to establish patient systemic access, measuring a biomarker parameter of the patient using a sensor; and controlling a pump to coordinate infusion of a drug through the patient's access with the biomarkers measured by the sensor. Again, for the purposes of illustration and without any intention of being limiting, the exemplary drug discussed herein can be a drug for affecting and/or controlling craving, for example, BUP, naloxone, naltrexone, a benzodiazepine or an antidepressant.

Figure 7:
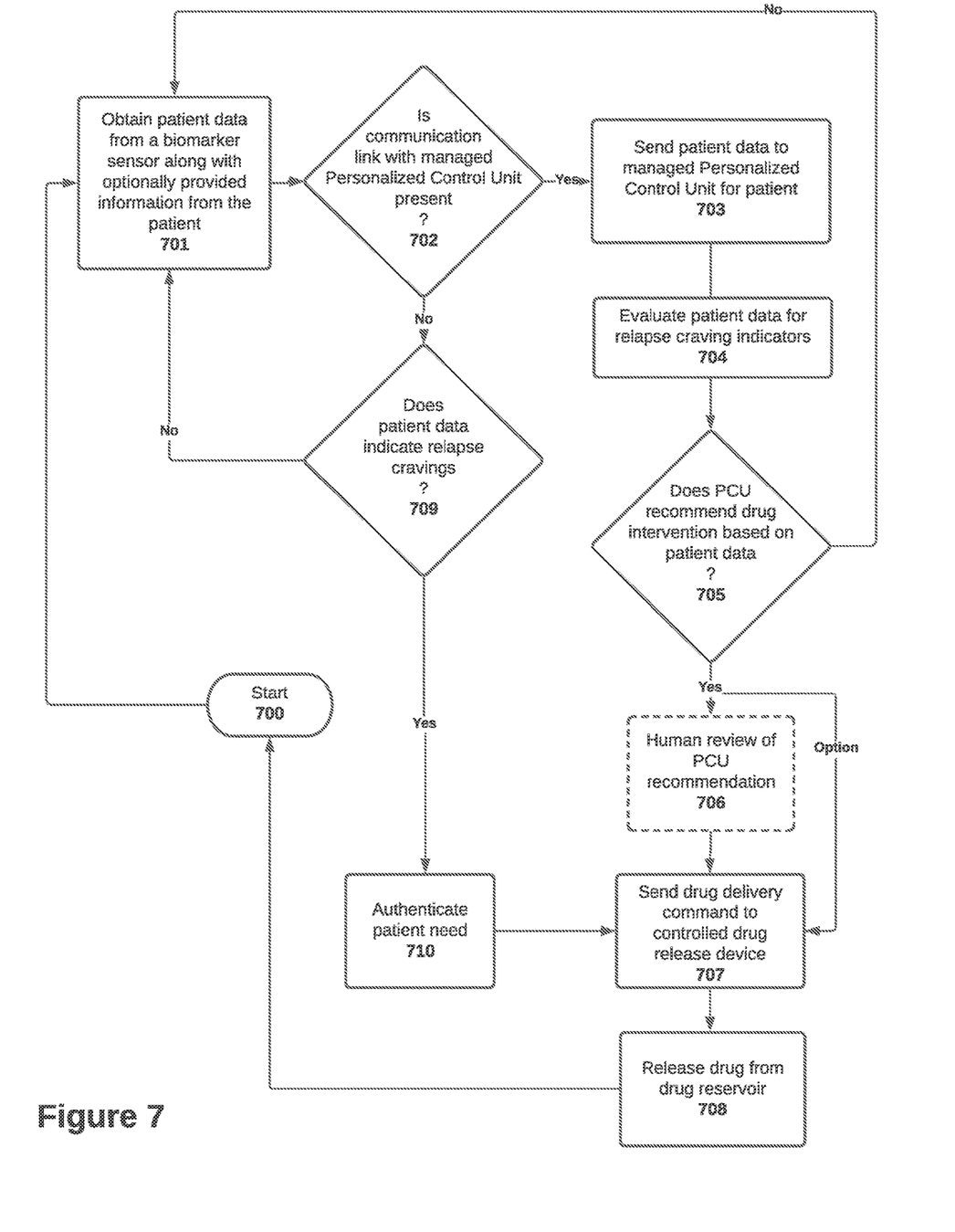
FIG. 7 illustrates a flow diagram of the decision tree used in accordance with one or more embodiments of the invention to facilitate drug release.

FIG. 7 illustrates a flow diagram of the decision tree used in accordance with one or more embodiments of the invention to facilitate drug release. In this instance, the drug delivery system comprises a personalized control unit, a health care provider unit, a controlled drug delivery pump containing a drug reservoir and supported by a housing to be placed on a patient and a network communication system. This drug delivery system enables health care professionals to remotely monitor and manage the drug recovery process by ensuring the patient is administered a proper dosage of BOU before cravings influence and then dictate the patient's behavior. When the system is operational (700), it obtains patient data from a biomarker sensor along with optionally provided information from the patient (701). If a communication link with a managed personal control unit is present (702), the patient data is sent to the managed personal control unit (703). The system defaults to this as the managed personalize control unit can evaluate the patient data as a whole and determine based on the patient's history, if the patient data indicates a reasonable probability of cravings potentially indicative of a relapse (704). This determination makes use in one embodiment of the invention of an AI learning algorithm that learns the patient's behavior patterns and biomarkers so it can assess the relapse probability and recommend a timely treatment. In other embodiments, AI learning is not used but the system is pre-programmed with software logic that evaluates the patient data and looks for certain biomarkers and/or behaviors in the patient so it can recommend a timely treatment. Based on the determination made, the personalize control until either recommends a drug intervention or does not (705). When a drug intervention is not recommended the system continues to monitor the patient and obtain patient data (701). When the system does recommend a drug intervention based on the patient data an optional step of human review of the personalized control until recommendation (705) may take place. Embodiments of the invention contemplate an open loop system wherein human review occurs (706) or a closed loop system where human review does not occur. If an approval is obtained or the system bypasses the human approval step, the system sends a drug delivery command to the controlled drug release device (707) that is dosed in an amount appropriate for the patient. The controlled drug release device releases the drug from the drug reservoir (708) and the system iterates to (700) continue monitoring the patient.

In instances where communication with the managed personalized control unit is absent, the system adopts a modified approach. If communication with the managed personalized control unit is absent (702), the system continues to monitor the patient to determine if the patient data indicates a potential relapse (709) due to cravings or otherwise. This aspect of one or more embodiments of the invention enables the system to function in a limited capacity when the patient is off the grid in some capacity or opts to disable network communications by virtue of their physical location or otherwise. When the system determined the patient is offline, there is a need for additional authentication to ensure the patient is not using the system to obtain additional drug dosages as addicts sometimes do. Therefore, before any drug treatment is administered, the system authenticates the patient need (710) for a treatment. This authentication step is configured to evaluate the actual patient need based on a variety of factors. For example, the patient's last dosage time, the patient's biomarker data, the patient's location, among other possible relevant inputs are all factors that may be considered in an authentication decision. Once authenticated, the system sends a drug delivery command to the controlled drug release device (707) and the drug is release from the drug reservoir (708).

A first sensor supported by the housing is configured to monitor the patient for predetermined biomarker levels and obtain a first biomarker data set. A second sensor is configured to allow patient assistance and/or input about biomarker levels in a second biomarker data set. A first communication device communicates the first biomarker data set to a processor within the personalized control until. A second communication device communicates the second biomarker data set to the processor as well. This second communication device is typically wireless but can utilize other communication mechanisms as well. The personalized control unit evaluates the first and second biomarker data set While the invention herein disclosed has been described by means of specific embodiments and applications thereof, numerous modifications and variations could be made thereto by those skilled in the art without departing from the scope of the invention set forth in the claims.

What is claimed is:

1. A system for identifying and remediating neonatal withdrawal symptoms comprising:
    a wearable device associated with a patient;
    a camera configured to record images of the patient;
    a data capture device associated with the wearable device and the camera, wherein said data capture device is configured to obtain biometric and behavioral data from said patient over progressive periods of time, the biometric and behavioral data including audio of the patient crying and images of the patient body movements;
    a patient evaluation module configured to:
        determine whether the audio of the patient crying corresponds to an excessive high-pitch above 800 Hz for less than five minutes or a continuous high-pitch above 800 Hz for more than five minutes,
        determine whether the detected body movements correspond to at least one of tremors, myoclonic jerks, or convulsions, and
        evaluate said biometric and behavioral data to make a probabilistic determination about a likelihood the patient is experiencing withdrawal symptoms associated with Neonatal Abstinence Syndrome (NAS), the evaluation taking into account the high-pitch crying determination and the detected body movements corresponding to the at least one of tremors, myoclonic jerks, or convulsions; and a mobile computing device configured to provide a result of said probabilistic determination and output a treatment recommendation.

2. The system of claim 1, wherein said patient evaluation module applies training inputs to a classification of said biometric and behavioral data.

3. The system of claim 2, wherein said probabilistic determination of said biometric and behavioral data comprises determining a weighted score based on said biometric and behavioral data.

4. The system of claim 3, wherein said treatment recommendation is based on a severity level dictated by said weighted score.

5. The system of claim 1, further comprising:
a drug delivery platform associated with said patient wherein said drug delivery platform is configured to administer a treatment drug based on said probabilistic determination.

6. The system of claim 5, wherein said drug delivery platform is a closed-loop system without physician approval.

7. The system of claim 5, wherein said drug delivery platform is an open-loop system requiring physician approval.

8. The system of claim 1, wherein said data capture device comprises at least one of the following: a blood oxygen monitor, a pulse sensor, a perspiration sensor, a camera with an associated image processing module, a temperature sensor, a respiratory monitor, an acoustic monitor, an electromyography device, and an accelerometer.

9. The system of claim 1, wherein said wearable device is a device attached to said patient's wrist.

10. The system of claim 9, wherein said wearable device comprises a chest hub worn by said patient.

11. The system of claim 1, wherein the camera is configured to record the biometric and behavioral data.

12. The system of claim 1, wherein the patient evaluation module is configured to distinguish between crying between 300 to 500 Hz in addition to crying above 800 Hz.

* * * * *

UNITED STATES PATENT AND TRADEMARK OFFICE
CERTIFICATE OF CORRECTION

| | | |
|---|---|---|
| PATENT NO. | : 12,138,007 B2 | Page 1 of 1 |
| APPLICATION NO. | : 17/528721 | |
| DATED | : November 12, 2024 | |
| INVENTOR(S) | : Shiva Sharareh | |

It is certified that error appears in the above-identified patent and that said Letters Patent is hereby corrected as shown below:

In the Specification

Column 1, Lines 1-3, after the Title, System for Identifying and Remediating Patient Withdrawal Symptoms, please add:
--GOVERNMENT LICENSE RIGHTS
This invention was made with government support under Grant Number 1R41DA049615-01A1 awarded by the National Institutes of Health (NIH), a part of the U.S. Department of Health and Human Services. The government has certain rights in the invention.--

Signed and Sealed this
Thirtieth Day of September, 2025

John A. Squires
*Director of the United States Patent and Trademark Office*